United States Patent
Fischer et al.

Patent Number: 5,481,002
Date of Patent: Jan. 2, 1996

[54] AZOLYL THERMOCHROMIC COMPOUNDS

[75] Inventors: Walter Fischer, Reinach; Beat Schmidhalter, Oberkirch; Heinz Wolleb, Marly, all of Switzerland

[73] Assignee: Ciba-Geigy Corporation, Tarrytown, N.Y.

[21] Appl. No.: 166,782

[22] Filed: Dec. 14, 1993

[30] Foreign Application Priority Data

Dec. 23, 1992 [CH] Switzerland ............... 3945/92

[51] Int. Cl.⁶ ............... C07D 249/12; C07D 249/04
[52] U.S. Cl. ............... 548/264.2; 548/307.1; 548/321.1; 548/255; 548/325.1; 548/366.1; 548/472; 548/484; 548/486
[58] Field of Search ............... 548/264.2, 307.1, 548/321.1, 325.1

[56] References Cited

U.S. PATENT DOCUMENTS

| | | | |
|---|---|---|---|
| 3,897,440 | 7/1975 | Beck et al. | 260/294.8 |
| 5,144,333 | 9/1992 | Mizuguchi et al. | 346/1.1 |

FOREIGN PATENT DOCUMENTS

| | | |
|---|---|---|
| 0155486 | 2/1985 | European Pat. Off. . |
| 353393 | 2/1990 | European Pat. Off. . |
| 401791 | 12/1990 | European Pat. Off. . |

OTHER PUBLICATIONS

Derw. Abst. 85–238056 [39] of EP 155,486, 1985.

*Primary Examiner*—Jacqueline Haley
*Attorney, Agent, or Firm*—George R. Dohmann; Michele A. Kovaleski

[57] ABSTRACT

There are disclosed compounds

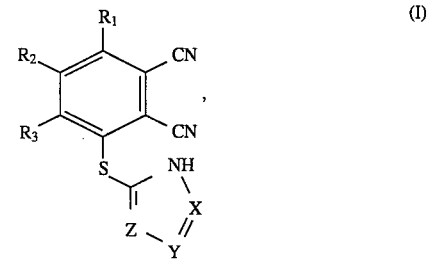

(I)

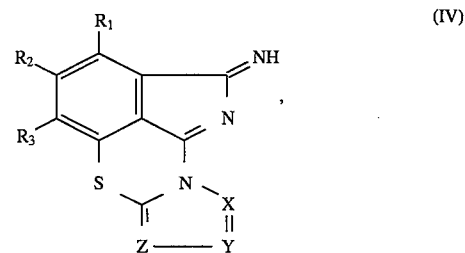

(IV)

wherein $R_1$, $R_2$ and $R_3$ are each independently of one another hydrogen, a $C_1$–$C_{12}$alkyl group, a $C_1$–$C_{12}$alkoxy group, a $C_5$–$C_8$cycloalkyl group, a $C_5$–$C_8$cycloalkoxy group, a $C_5$–$C_8$cycloalkylthio group, a $C_6$–$C_{10}$aryl group, a $C_6$–$C_{10}$aryloxy group, a $C_6$–$C_{10}$arylthio group, nitro, halogen, cyano, —COOH, —COOR$_7$, —NR$_8$R$_9$ or —CONR$_8$R$_9$, where $R_7$ is $C_1$–$C_{20}$alkyl, $C_5$–$C_8$acycloalkyl, phenyl or phenyl-$C_1$–$C_4$alkyl, and $R_8$ and $R_9$ are each independently of the other hydrogen, $C_1$–$C_8$alkyl, phenyl or phenyl-$C_1$–$C_4$alkyl, X is nitrogen or CR$_4$, Y is nitrogen or CR$_5$ and Z is nitrogen or CR$_6$, and $R_4$, $R_5$ and $R_6$ are each independently of one another hydrogen, a straight-chain or branched $C_1$–$C_{12}$alkyl group or a $C_6$–$C_{10}$aryl group, with the proviso that, if X is CR$_4$ and Y is CR$_5$ and Z is nitrogen or CR$_6$, or if Y is CR$_5$ and Z is CR$_6$ and X is nitrogen or CR$_4$, then each pair of substituents $R_4$ and $R_5$ and $R_5$ and $R_6$ form a group —CH=C(R$_{10}$)—C(R$_{11}$)=CH— or a tetramethylene group, wherein $R_{10}$ and $R_{11}$ are each independently of the other hydrogen, $C_1$–$C_6$alkyl, phenyl or phenyl-$C_1$–$C_4$alkyl. The compounds are suitable for use as active components in thermal information recording systems, especially for laser-optical information recording media.

14 Claims, No Drawings

AZOLYL THERMOCHROMIC COMPOUNDS

The present invention relates to novel thermochromic compounds, to their preparation and to the use thereof in thermochromic systems for contrast formation, light absorption and for recording information, as well as to thermochromic recording materials which contain the novel compounds as thermochromic components.

Laser-optical information recording media in the form of CD-compatible WORM systems (write once read many) form the subject matter of, inter alia, EP-A-0 353 393. In this publication, the information is written by means of a change in the absorption or reflectance in the memory-active +recording layer induced by a laser beam. In order to be able to use the simple diode laser in the near infra-red range (NIR range), the memory-active layer contains dyes that absorb IR radiation, typically cyanine dyes. The information dot obtained after irradiation therefore has a lower absorption or increased reflectance that can be optically read out.

Surprisingly, novel irreversibly thermochromic compounds have now been found that exhibit no absorption bands in the NIR range and which, when subjected to heat or heat radiation, are converted into products which have strong absorption bands in the NIR range. The compounds therefore have excellent suitability for memory-active layers in laser-optical recording and reading-out techniques, especially using diode lasers and laser light in the NIR range, utilising the increased absorption or lowered reflectance for reading out the written information.

In one of its aspects, the invention relates to compounds of formula I

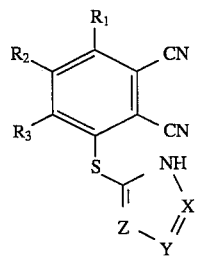

wherein $R_1$, $R_2$ and $R_3$ are each independently of one another hydrogen, a straight-chain or branched $C_1$–$C_{12}$alkyl group, which is unsubstituted or substituted by alkoxy, alkylthio, aryloxy, arylthio, halogen, —CN, —COOH, —COOR$_7$, —NR$_8$R$_9$ or —CONR$_8$R$_9$, a $C_1$–$C_{12}$alkoxy group in which the alkyl moiety is straight-chain or branched and unsubstituted or substituted by alkoxy, alkylthio, aryloxy, arylthio, halogen, —CN, —COOH, —COOR$_7$, —NR$_8$R$_9$ or —CONR$_8$R$_9$, a $C_1$–$C_{12}$alkylthio group in which the alkyl moiety is straight-chain or branched and unsubstituted or substituted by alkoxy, alkylthio, aryloxy, arylthio, halogen, —CN, —COOH, —COOR$_7$, —NR$_8$R$_9$ or —CONR$_8$R$_9$, a $C_5$–$C_8$cycloalkyl group which is unsubstituted or substituted by alkyl, alkoxy, alkylthio, aryloxy, arylthio, halogen, —CN, —COOH, —COOR$_7$, —NR$_8$R$_9$ or —CONR$_8$R$_9$, a $C_5$–$C_8$cycloalkoxy group which is unsubstituted or substituted by alkyl, alkoxy, alkylthio, aryloxy, arylthio, halogen, —CN, —COOH, —COOR$_7$, —NR$_8$R$_9$ or —CONR$_8$R$_9$, a $C_5$–$C_8$cycloalkylthio group which is unsubstituted or substituted by alkyl, alkoxy, alkylthio, aryloxy, arylthio, halogen, —CN, —COOH, —COOR$_7$, —NR$_8$R$_9$ or —CONR$_8$R$_9$, a $C_6$–$C_{10}$aryl group which is unsubstituted or substituted by alkyl, alkoxy, alkylthio, aryloxy, arylthio, halogen, —CN, —COOH, —COOR$_7$, —NR$_8$R$_9$ or —CONR$_8$R$_9$, a $C_6$–$C_{10}$aryloxy group in which the aryl moiety is unsubstituted or substituted by alkyl, alkoxy, alkylthio, phenyl, phenoxy, phenylthio, halogen, —CN, —COOH, —COOR$_7$, —NR$_8$R$_9$ or —CONR$_8$R$_9$, a $C_6$–$C_{10}$arylthio group in which the aryl moiety is unsubstituted or substituted by alkyl, alkoxy, alkylthio, phenyl, phenoxy, phenylthio, halogen, —CN, —COOH, —COOR$_7$, —NR$_8$R$_9$ or —CONR$_8$R$_9$ or $R_1$, $R_2$, $R_3$ are independently of one another nitro, halogen, cyano, —COOH, —COOR$_7$, —NR$_8$R$_9$ or —CONR$_8$R$_9$, and wherein $R_7$ is $C_1$–$C_{20}$alkyl, $C_5$–$C_8$cycloalkyl, phenyl or phenyl-$C_1$–$C_4$alkyl, and $R_8$ and $R_9$ are each independently of the other hydrogen, $C_1$–$C_8$alkyl, phenyl or phenyl-$C_1$–$C_4$alkyl, X is nitrogen or $CR_4$, Y is nitrogen or $CR_5$ and Z is nitrogen or $CR_6$, and $R_4$, $R_5$ and $R_6$ are each independently of one another hydrogen, a straight-chain or branched $C_1$–$C_{12}$alkyl group which is unsubstituted or substituted by alkoxy, alkylthio, aryloxy, arylthio, halogen, —CN, —COOH, —COOR$_7$, —NR$_8$R$_9$ or —CONR$_8$R$_9$, or a $C_6$–$C_{10}$aryl group which is unsubstituted or substituted by alkyl, alkoxy, alkylthio, aryloxy, arylthio, halogen, —CN, —COOH, —COOR$_7$, —NR$_8$R$_9$ or —CONR$_8$R$_9$, and with the proviso that, if X is $CR_4$ and Y is $CR_5$ and Z is nitrogen or $CR_6$, or if Y is $CR_5$ and Z is $CR_6$ and X is nitrogen or $CR_4$, then each pair of substituents $R_4$ and $R_5$ and $R_5$ and $R_6$ forms a group

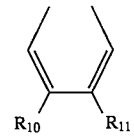

or a tetramethylene group, wherein $R_{10}$ and $R_{11}$ are each independently of the other hydrogen, $C_1$–$C_6$alkyl, phenyl or phenyl-$C_1$–$C_4$alkyl.

Typical straight-chain or branched $C_1$–$C_{12}$alkyl groups which may occur as substituents $R_1$, $R_2$ and $R_3$, or which may be present as alkoxy or alkylthio groups in the substituents $R_1$, $R_2$ and $R_3$, are methyl, ethyl, n-propyl, isopropyl, n-butyl, isobutyl, sec-butyl, tert-butyl, n-pentyl, 2-pentyl, n-hexyl, n-heptyl, n-octyl, isooctyl, nonyl, decyl, undecyl and dodecyl. Among these straight-chain or branched $C_1$–$C_{12}$alkyl groups represented by, or occurring in, the substituents $R_1$, $R_2$ and $R_3$, straight-chain or branched $C_1$–$C_8$alkyl groups and, more particularly, $C_1$–$C_4$alkyl groups, are preferred.

Where $R_1$, $R_2$ and $R_3$ are defined as $C_5$–$C_8$cycloalkyl, $C_5$–$C_8$cycloalkoxy and $C_5$–$C_8$cycloalkylthio, cycloalkyl is preferably cyclohexyl.

Where $R_1$, $R_2$ and $R_3$ are defined as $C_6$–$C_{10}$aryl, $C_6$–$C_{10}$aryloxy and $C_6$–$C_{10}$arylthio, $C_6$–$C_{10}$aryl is preferably phenyl or naphthyl and, most preferably, phenyl.

$R_1$, $R_2$ and $R_3$ defined as $C_1$–$C_{12}$alkyl, $C_1$–$C_{12}$alkoxy and $C_1$–$C_{12}$alkythio may be substituted by one to three members, preferably by one member, selected from the group consisting of alkoxy, alkylthio, aryl, aryloxy, arylthio, halogen, —CN, —COOH, —COOR$_7$, —NR$_8$R$_9$ and —CONR$_8$R$_9$. The alkyl moieties of the alkoxy and alkythio groups may contain 1 to 12 carbon atoms. Preferably, however, these alkyl groups contain 1 to 6 and, most preferably, 1 to 4 carbon atoms. Aryl in the aryl, aryloxy and arylthio groups may contain 6 to 10 carbon atoms and is typically phenyl or naphthyl. The preferred meaning of aryl in these groups is phenyl. Halogen is fluoro, chloro, bromo or iodo, preferably fluoro, chloro or bromo. The substituents $R_7$, $R_8$ and R occurring in the groups —COOR$_7$, —NR$_8$R$_9$ and —CONR$_8$R$_9$ are preferably $C_1$–$C_8$alkyl, phenyl or phenyl-$C_1$-$C_4$alkyl, while phenyl and the phenyl moiety of phenyl-$C_1$-$C_4$alkyl may be substituted by customary substituents, including $C_1$-$C_4$alkyl, $C_1$-$C_4$alkoxy, halogen or nitro.

$R_1$, $R_2$ and $R_3$ defined as $C_5$-$C_8$cycloalkyl, $C_5$-$C_8$cycloalkoxy, $C_5$-$C_8$cycloalkylthio, $C_6$-$C_{10}$aryl, $C_6$-$C_{10}$aryloxy and $C_6$-$C_{10}$arylthio may be substituted by one to three members, preferably by one member, selected from the group consisting of alkyl, alkoxy, alkylthio, aryl, aryloxy, arylthio, halogen, —CN, —COOH, —$COOR_7$, —$NR_8R_9$ or —$CONR_8R_9$. The alkyl, alkoxy and alkylthio groups may contain 1 to 12 carbon atoms. Preferably, however, these alkyl, alkoxy and alkylthio groups contain 1 to 8 carbon atoms and, most preferably, 1 to 4 carbon atoms. Aryl in the aryl, aryloxy and arylthio groups may contain 6 to 10 carbon atoms and is typically phenyl or naphthyl. The preferred meaning of aryl in these groups is phenyl. Halogen is preferably fluoro, chloro or bromo, most preferably fluoro or chloro. The substituents $R_7$, $R_8$ and $R_9$ occurring in the groups —$COOR_7$, —$NR_8R_9$ and —$CONR_8R_9$ are preferably $C_1$-$C_8$alkyl, phenyl or phenyl-$C_1$-$C_4$alkyl, while phenyl and the phenyl moiety of phenyl-$C_1$-$C_4$alkyl may be substituted by customary substituents, including $C_1$-$C_4$alkyl, $C_1$-$C_4$alkoxy, halogen or nitro.

$R_1$, $R_2$ und $R_3$ are preferably each independently of one another hydrogen, a $C_1$-$C_8$alkyl group which is unsubstituted or substituted by $C_1$-$C_4$alkoxy, $C_1$-$C_4$alkylthio, phenyl, phenoxy, phenylthio, fluoro, chloro, bromo, —CN, —COOH, —$COOR_7$, —$NR_8R_9$ or —$CONR_8R_9$, a $C_1$-$C_8$alkoxy group in which the the alkyl moiety is straight-chain or branched and is unsubstituted or substituted by $C_1$-$C_4$alkoxy, $C_1$-$C_4$alkylthio, phenyl, phenoxy, phenylthio, fluoro, chloro, bromo, —CN, —COOH, —$COOR_7$, —$NR_8R_9$ or —$CONR_8R_9$, a $C_1$-$C_8$alkylthio group in which the alkyl moiety is straight-chain or branched and is unsubstituted or substituted by $C_1$-$C_4$alkoxy, $C_1$-$C_4$alkylthio, phenyl, phenoxy, phenylthio, fluoro, chloro, bromo, —CN, —COOH, —$COOR_7$, —$NR_8R_9$ or —$CONR_8R_9$, a cyclohexyl group which is unsubstituted or substituted by $C_1$-$C_4$alkyl, $C_1$-$C_4$alkoxy, $C_1$-$C_4$alkylthio, phenyl, phenoxy, phenylthio, fluoro, chloro, bromo, —CN, —COOH, —$COOR_7$, —$NR_8R_9$ or —$CONR_8R_9$, a cyclohexyloxy group which is unsubstituted or substituted by $C_1$-$C_4$alkyl, $C_1$-$C_4$alkoxy, $C_1$-$C_4$alkylthio, phenyl, phenoxy, phenylthio, fluoro, chloro, bromo, —CN, —COOH, —$COOR_7$, —$NR_8R_9$ or —$CONR_8R_9$, a cyclohexylthio group which is unsubstituted or substituted by $C_1$-$C_4$alkyl, $C_1$-$C_4$alkoxy, $C_1$-$C_4$alkylthio, phenyl, phenoxy, phenylthio, fluoro, chloro, bromo, —CN, —COOH, —$COOR_7$, —$NR_8R_9$ or —$CONR_8R_9$, a phenyl or naphthyl group which is unsubstituted or substituted by $C_1$-$C_4$alkyl, $C_1$-$C_4$alkoxy, $C_1$-$C_4$alkylthio, phenyl, phenoxy, phenylthio, fluoro, chloro, bromo, —CN, —COOH, —$COOR_7$, —$NR_8R_9$ or —$CONR_8R_9$, a phenoxy or naphthoxy group which is unsubstituted or substituted by $C_1$-$C_4$alkyl, $C_1$-$C_4$alkoxy, $C_1$-$C_4$alkylthio, phenyl, phenoxy, phenylthio, fluoro, chloro, bromo, —CN, —COOH, —$COOR_7$, —$NR_8R_9$ or —$CONR_8R_9$, a phenylthio or naphthylthio group which is unsubstituted or substituted by $C_1$-$C_4$alkyl, $C_1$-$C_4$alkoxy, $C_1$-$C_4$alkylthio, phenyl, phenoxy, phenylthio, fluoro, chloro, bromo, —CN, —COOH, —$COOR_7$, —$NR_8R_9$, or fluoro, chloro, bromo, nitro, cyano, —COOH, —$COOR_6$, —$NR_7R_8$ or —$CONR_7R_8$, and wherein $R_7$ is $C_1$-$C_8$alkyl or phenyl and $R_8$ and $R_9$ are each independently of the other hydrogen, $C_1$-$C_8$alkyl, phenyl or phenyl-$C_1$-$C_4$alkyl.

Most preferably $R_1$, $R_2$ and $R_3$ are each independently of one another hydrogen, a $C_1$-$C_4$alkyl group which is unsubstituted or substituted by $C_1$-$C_4$alkoxy, $C_1$-$C_4$alkylthio, phenyl, phenoxy, phenylthio, fluoro, chloro, bromo, —CN, —COOH, —$COOR_7$, —$NR_8R_9$ or —$CONR_8R_9$, a $C_1$-$C_4$alkoxy group in which the alkyl moiety is straight-chain or branched and which is unsubstituted or substituted by $C_1$-$C_4$alkoxy, $C_1$-$C_4$alkylthio, phenyl, phenoxy, phenylthio, fluoro, chloro, bromo, —CN, —COOH, —$COOR_7$, —$NR_8R_9$ or —$CONR_8R_9$, a $C_1$-$C_4$alkylthio group in which the alkyl moiety is straight-chain or branched and which is unsubstituted or substituted by $C_1$-$C_4$alkoxy, $C_1$-$C_4$alkylthio, phenyl, phenoxy, phenylthio, fluoro, chloro, bromo, —CN, —COOH, —$COOR_7$, —$NR_8R_9$ or —$CONR_8R_9$, a cyclohexyl group which is unsubstituted or substituted by $C_1$-$C_4$alkyl, $C_1$-$C_4$alkoxy, $C_1$-$C_4$alkylthio, phenyl, phenoxy, phenylthio, fluoro, chloro, bromo, —CN, —COOH, —$COOR_7$, —$NR_8R_9$ or —$CONR_8R_9$, a cyclohexyloxy group which is unsubstituted or substituted by $C_1$-$C_4$alkyl, $C_1$-$C_4$alkoxy, $C_1$-$C_4$alkylthio, phenyl, phenoxy, phenylthio, fluoro, chloro, bromo, —CN, —COOH, —$COOR_7$, —$NR_8R_9$ or —$CONR_8R_9$, a cyclohexylthio group which is unsubstituted or substituted by $C_1$-$C_4$alkyl, $C_1$-$C_4$alkoxy, $C_1$-$C_4$alkylthio, phenyl, phenoxy, phenylthio, fluoro, chloro, bromo, —CN, —COOH, —$COOR_7$, —$NR_8R_9$ or —$CONR_8R_9$, a phenyl or naphthyl group which is unsubstituted or substituted by $C_1$-$C_4$alkyl, $C_1$-$C_4$alkoxy, $C_1$-$C_4$alkylthio, phenyl, phenoxy, phenylthio, fluoro, chloro, bromo, —CN, —COOH, —$COOR_7$, —$NR_8R_9$ or —$CONR_8R_9$, a phenoxy or naphthoxy group which is unsubstituted or substituted by $C_1$-$C_4$alkyl, $C_1$-$C_4$alkoxy, $C_1$-$C_4$alkylthio, phenyl, phenoxy, phenylthio, fluoro, chloro, bromo, —CN, —COOH, —$COOR_7$, —$NR_8R_9$ or —$CONR_8R_9$, a phenylthio or naphthylthio group which is unsubstituted or substituted by $C_1$-$C_4$alkyl, $C_1$-$C_4$alkoxy, $C_1$-$C_4$alkylthio, phenyl, phenoxy, phenylthio, fluoro, chloro, bromo, —CN, —COOH, —$COOR_7$, —$NR_8R_9$ or —$CONR_8R_9$, or fluoro, chloro, bromo, nitro, cyano, —COOH, —$COOR_6$, —$NR_7R_8$ or —$CONR_7R_8$, and wherein $R_7$ is $C_1$-$C_4$alkyl or phenyl, and $R_8$ and $R_9$ are each independently of the other hydrogen, $C_1$-$C_4$alkyl, phenyl or benzyl.

The azolyl group of formula

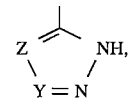

present in the compounds of formula I, wherein X is nitrogen or $CR_4$, Y is nitrogen or $CR_5$ and Z is nitrogen or $CR_6$, and $R_4$, $R_5$ and $R_6$ are as defined in claim 1, may be pyrrol-2-yl, imidazol-2-yl, imidazol-4-yl, imidazol-5-yl, pyrazol-3-yl, pyrazol-5-yl, 1H-1,2,3-triazol-5-yl, 2H-1,2,3-triazol-5-yl, 3H-1,2,3-triazol-5-yl, 1H-1,2,4-triazol-5-yl, 2H-1,2,4-triazol-5-yl, 4H-1,2,4-triazol-5-yl, 1H-1,2,3,4-tetrazol-5-yl, 2H-1,2,3,4-tetrazol-5-yl, indol-2-yl, isoindol-1-yl, benzimidazol-2-yl, benzpyrazol-3-yl, 4,5,6,7-tetrahydroindol-2-yl, 4,5,6,7-tetrahydroisoindol-1-yl, 4,5,6,7-tetrahydrobenzimidazol-2-yl, 4,5,6,7-tetrahydrobenzpyrazol-3-yl, each unsubstituted or substituted by $R_4$, $R_5$ and $R_6$, in which radicals the fused benzene rings or tetrahydrobenzene rings may be substituted by $R_{10}$ and $R_{11}$, which have the meanings given in claim 1 in the definition of formula I.

The substituents $R_4$, $R_5$ and $R_6$ in the groups $CR_4$, $CR_5$ and $CR_6$ present in the azole radicals that are not fused with benzene nuclei may each independently of one another be a straight-chain or branched $C_1$–$C_{12}$alkyl group which is unsubstituted or substituted by alkoxy, alkylthio, aryloxy, arylthio, halogen, —CN, —COOH, —COOR$_7$, —NR$_8$R$_9$ or —CONR$_8$R$_9$, or is a $C_6$–$C_{10}$aryl group which is unsubstituted or substituted by alkyl, alkoxy, alkylthio, aryloxy, arylthio, halogen, —CN, —COOH, —COOR$_7$, —NR$_8$R$_9$ or —CONR$_8$R$_9$. When X is $CR_4$, Y is $CR_5$ and Z is $CR_6$, then $R_4$, $R_5$ and $R_6$ are each independently of one another $C_1$–$C_4$alkyl, $C_1$–$C_4$haloalkyl or phenyl, which haloalkyl group may contain one or more than one halogen atom, and halogen is fluoro, chloro or bromo and, preferably, fluoro or chloro. A preferred haloalkyl group is trifluoromethyl. The substituents $R_{10}$ and $R_{11}$ of the group

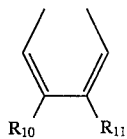

formed by $R_4$ and $R_5$ together or by $R_5$ and $R_6$ together are preferably hydrogen, so that the group formed by $R_4$ and $R_5$ together or by $R_5$ and $R_6$ together is preferably a 1,3-butadienylene group.

Preferred azolyl radicals are imidazol-2-yl and 1,2,4-triazol-3-yl.

A further preferred group of compounds of formula I embraces those in which $R_4$, $R_5$ and $R_6$ are each independently of one another $C_1$–$C_4$alkyl, $C_1$–$C_4$haloalkyl or phenyl, or $R_4$ and $R_5$, or $R_5$ and $R_6$, each taken together, are a 1,3-butadienylene group, and $R_1$, $R_2$ and $R_3$ are as defined for formula I, including the preferred meanings subsequently given.

Also preferred are compounds of formula I in which X is $CR_4$, Y is $CR_5$ and Z is nitrogen, and $R_4$ and $R_5$, as well as $R_1$, $R_2$ and $R_3$, are as defined above for formula I, including the preferred meanings subsequently given. Among these compounds, those compounds are in turn especially preferred in which $R_4$ und $R_5$ are each independently of the other $C_1$–$C_4$alkyl, $C_1$–$C_4$haloalkyl or phenyl, or $R_4$ and $R_5$, taken together, are a 1,3-butadienylene, and $R_1$, $R_2$ and $R_3$ are as defined for formula I, including the preferred meanings subsequently given.

Futher preferred compounds of formula I are those wherein X is $CR_4$, Y is nitrogen and Z is $CR_6$, and $R_4$ and $R_6$, as well as $R_1$, $R_2$ and $R_3$, are as defined for formula I, including the preferred meanings subsequently given. Among these compounds, those compounds are in turn especially preferred in which $R_4$ and $R_6$ are each independently of the other hydrogen, $C_1$–$C_4$alkyl, $C_1$–$C_4$haloalkyl or phenyl.

Another group of preferred compounds of formula I embraces those in which X is nitrogen, Y is $CR_5$ and Z is $CR_6$, and $R_5$ and $R_6$, as well as $R_1$, $R_2$ and $R_3$ are as defined for formula I, including the preferred meanings subsequently given. Among these compounds, those compounds are in turn especially preferred in which $R_5$ and $R_6$ are each independently of the other hydrogen, $C_1$–$C_4$alkyl, $C_1$–$C_4$haloalkyl or phenyl, or $R_5$ and $R_6$, taken together, are a 1,3-butadienylene radical, and $R_1$, $R_2$ and $R_3$ are as defined for formula I, including the preferred meanings subsequently given.

Yet another preferred group of compounds of formula I embraces those in which X and Y are nitrogen, and Z is $CR_6$, an $R_6$ as well as $R_1$, $R_2$ and $R_3$ are as defined for formula I, including the preferred meanings subsequently given. Among these compounds, those compounds are in turn especially preferred in which $R_6$ is hydrogen, $C_1$–$C_4$alkyl, $C_1$–$C_4$haloalkyl or phenyl, and $R_1$, $R_2$ and $R_3$ are as defined for formula I, including the preferred meanings subsequently given.

Those compounds of formula I are also preferred in which X, Y and Z are nitrogen, and $R_1$, $R_2$ and $R_3$ are as defined for formula I, including the preferred meanings given hereinafter.

As stated above, $R_1$, $R_2$ and $R_3$ may each independently of one another have the meanings as indicated above. In a particular embodiment of the invention, those compounds of formula I are preferred in which $R_1$ and $R_3$ are hydrogen and $R_2$, X, Y and Z are as defined in connection with the definition of the general formula I.

In a further preferred subgroup of compounds of the general formula I, $R_1$ and $R_3$ are hydrogen and $R_2$ is $C_1$–$C_8$alkyl, $C_1$–$C_8$alkoxy, $C_1$–$C_8$alkylthio, cyclohexyl, cyclohexyloxy, cyclohexylthio, phenyl, phenoxy, phenylthio, fluoro, chloro, bromo, nitro, cyano, —COOH, —COOR$_7$, —NR$_8$R$_9$ or —CONR$_8$R$_9$, wherein $R_7$ is $C_1$–$C_8$alkyl, phenyl-$C_1$–$C_4$alkyl or phenyl, and $R_8$ and $R_9$ are each independently of the other hydrogen, $C_1$–$C_8$alkyl, phenyl or phenyl-$C_1$–$C_4$alkyl, X is nitrogen or $CR_4$, Y is nitrogen or $CR_5$ and Z is nitrogen or $CR_6$, where $R_4$, $R_5$ and $R_6$ are each independently of one another hydrogen, $C_1$–$C_4$alkyl, $C_1$–$C_4$haloalkyl or phenyl, and with the proviso that, when X is $CR_4$ and Y is $CR_5$ and Z is nitrogen or $CR_6$, or if Y is $CR_5$ and Z is $CR_6$ and X is nitrogen or $CR_4$, then each pair of substituents $R_4$ and $R_5$ or $R_5$ and $R_6$ may also be a 1,3-butadienylene group.

In a further particularly preferred subgroup of compounds of the general formula I, $R_1$ and $R_3$ are hydrogen and $R_2$ is $C_1$–$C_4$alkyl, $C_1$–$C_4$alkoxy, $C_1$–$C_4$alkylthio, cyclohexyl, cyclohexyloxy, cyclohexylthio, phenyl, phenoxy, phenylthio, fluoro, chloro, bromo, nitro, cyano, —COOH, —COOR$_7$, —NR$_8$R$_9$ or —CONR$_8$R$_9$, wherein $R_7$ is $C_1$–$C_4$alkyl, phenyl or benzyl, and $R_8$ and $R_9$ are each independently of the other hydrogen, $C_1$–$C_4$alkyl, phenyl or benzyl, X is nitrogen or $CR_4$, Y is nitrogen or $CR_5$ and Z is nitrogen or $CR_6$, wherein $R_4$, $R_5$ and $R_6$ are each independently of one another hydrogen, $C_1$–$C_4$alkyl, $C_1$–$C_4$haloalkyl or phenyl, and with the proviso that, when X is $CR_4$ and Y is $CR_5$ and Z is nitrogen or $CR_6$, or if Y is $CR_5$ and Z is $CR_6$ and X is nitrogen or $CR_4$, then each pair of substituents $R_4$ and $R_5$ or $R_5$ and $R_6$ may also be a 1,3-butadienylene group.

Particularly preferred compounds of formula I are those wherein $R_1$ and $R_3$ are hydrogen, $R_2$ is hydrogen, nitro, $C_1$–$C_4$alkylthio or phenylthio, in which the phenyl moiety may be substituted by $C_1$–$C_4$alkyl, $C_1$–$C_4$alkoxy or $C_1$–$C_4$alkylthio, X is $CR_4$, Y is $CR_5$ or nitrogen, and Z is nitrogen, and $R_4$ and $R_5$ are each independently of the other hydrogen, $C_1$–$C_4$alkyl, $C_1$–$C_4$haloalkyl, phenyl or, taken together, are a group

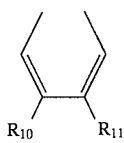

wherein $R_{10}$ and $R_{11}$ are each independently of the other hydrogen or $C_1$-$C_4$alkyl.

In another of its aspects, the invention relates to a process for the preparation of the compounds of formula I. This process comprises reacting a substituted phthalodinitrile of formula II

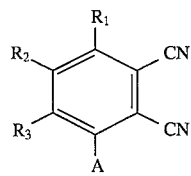

wherein $R_1$, $R_2$ and $R_3$ are as defined for formula I and A is halogen or a nitro group, in an inert solvent and in the presence of a base, with an azole of the general formula III

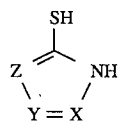

wherein X, Y and Z are as defined for formula I.

Some of the starting materials of formulae II and III are known and some are novel compounds. The novel compounds of formulae II or III can be prepared in a manner analogous to that for the preparation of already known compounds.

Preferred starting materials of formula II are those wherein A is a nitro group.

Inert solvents which may suitably be used are aliphatic and aromatic hydrocarbons such as hexane, cyclohexane, toluene, xylene and mesitylene; aliphatic and aromatic halogenated hydrocarbons, including methylene chloride, chloroform, carbon tetrachloride, trichloroethane, tetrachloroethane, trichloroethylene, chlorobenzene and dichlorobenzene; ethers, including diethyl ether, dibutyl ether, diisobutyl ether, tetrahydrofuran and dioxane; and also dimethyl sulfoxide and acid amide derivatives, typically N,N-dimethylformamide, N,N-dimethylacetamide and N-methyl-2-pyrrolidone; nitriles, such as acetonitrile; ketones such as acetone and methyl ethyl ketone; carboxylates such as ethyl acetate. Preferred solvents are dimethyl sulfoxide, N,N-dimethylformamide, N-methyl-2-pyrrolidone, tetrahydrofuran and dioxane.

Particularly suitable bases are the hydroxides, carbonates and hydrogencarbonates of alkali metals and alkaline earth metals, including sodium hydroxide, potassium hydroxide, sodium carbonate, sodium hydrogencarbonate, potassium hydroxide, potassium carbonate, potassium hydrogencarbonate, calcium hydroxide, calcium carbonate and calcium hydrogencarbonate; and also tertiary amines such as triethylamine, pyridine and quinoline. Preferred bases are potassium carbonate, triethylamine and pyridine. A particularly preferred base is potassium carbonate.

The reaction can be carried out at room temperature or below or at elevated temperature. Suitable reaction temperatures are in the range from 0° C. to 100° C. It is preferred to carry out the reaction in the temperature range from 0° C. to 60° C. In another of its aspects, the invention relates to compounds of the general formula IV

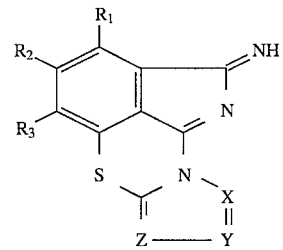

wherein $R_1$, $R_2$, $R_3$, X, Y and Z are as defined for formula I.

The preferred meanings of $R_1$, $R_2$, $R_3$, X, Y and Z correspond to those indicated for these substituents in connection with the definition of formula I.

The compounds of the general formula IV can be prepared in the practice of this invention by heating a compound of formula I to a temperature in the range from 75° C. to 300° C., preferably from 90° C. to 160° C.

Heating can be carded out in the absence or presence of an inert solvent. Typical examples of suitable solvents are aliphatic and aromatic hydrocarbons such as hexane, heptane, octane, toluene, xylene, mesitylene, tetrahydronaphthalene and decahydronaphthalene, as well as aliphatic and aromatic halogenated hydrocarbons such as trichloroethane, tetrachloroethane, trichloroethylene, chlorobenzene and dichlorobenzene. Preferred solvents are toluene, xylene, mesitylene and o-dichlorobenzene.

If the process for the preparation of a compound of the general formula IV is carried out in an inert solvent, the compounds of formula IV usually precipitate from the reaction solution in solid form and can be isolated in simple manner by filtration. If the process is carried out without a solvent, then the compound of formula I is conveniently heated under vacuum and the compound of formula IV is isolated from the reaction mixture by sublimation. The heating time can vary in accordance with the compound of formula I and the temperature and is normally in the range from 1 minute to 10 hours and, preferably, from 1 to 5 hours.

The compounds of formulae I and IV are crystalline and colourless to pale yellow. They are soluble in solvents and in polymers. In addition, the compounds of formulae I and IV are irreversibly thermochromic, i.e. when exposed to heat or heat radiation they undergo a marked change in colour ranging from colourless to pale yellow through green, brown to black. The action of heat or heat radiation causes the light absorption of the compounds of formulae I and IV to shift towards longer wavelengths. The rate of conversion is surprisingly high and, depending on the mount and thickness of the sample and on the intensity of the heat irradiation, can be less than 3 seconds. The thermochromic conversion is irreversible.

The compounds of formulae I and IV therefore have excellent suitability as heat-sensitive active components for different techniques of recording information using heat or heat radiation, or as active components in thermochromic display elements.

In yet another of its aspects, the invention relates to a material for the optical recording and storage of information, said material comprising a substrate coated with at least one layer of at least one of the compounds of formulae I and IV without or together with a binder as memory-active layer. The substrate is preferably transparent.

Suitable substrates are typically metals, alloys, glasses, minerals, ceramics, paper and thermoset or thermoplastic materials. The substrate may have a thickness of 0.01 mm to 1 cm, preferably of 0.1 mm to 0.5 cm. Preferred substrates are glasses and homopolyeric or copolymeric plastic materials. Suitable plastic materials include thermoplastic polycarbonates, polyamides, polyesters, polyacrylates and polymethacrylates, polyurethanes, polyolefins, polyvinyl chloride, polyvinylidene fluoride, polyimides, thermoset polyesters and epoxy resins.

The substrates can be prepared by the mixing and shaping methods customarily used for thermosetting and thermoplastic materials, typically casting, moulding, injection moulding and extrusion methods.

The substrate may be coated with one or more than one layer, typically with 1 to 10, preferably 1 to 5 and, most preferably, 1 to 3, layers of identical or different compounds of formula I. The number of layers and further layers will depend mainly on the desired optical density of the layer arrangement, which must ensure a sufficient transmission at the wavelength used for recording.

The thickness of the layer of compounds of formula I and/or IV is typically 100 to 3000 Å, preferably 100 to 2000 Å and, most preferably, 200 to 1500 Å. If a binder is used, the layer thickness may be from 0.1 to 500 μm, preferably from 1 to 200 μm and, most preferably, from 1 to 100 μm.

The memory-active layer or the substrate can be coated with a reflective layer which has a thickness of typically 100 to 5000 Å, preferably 100 to 3000 Å and, most preferably, 300 to 1500 Å. Particularly suitable reflective materials are metals which reflect the laser light used for recording and reproduction well. A reflective layer of aluminium or gold is especially preferred on account of the high reflectivity and the ease with which it can be prepared.

The topmost layer, depending on the layer structure, for example the reflective layer, the memory-active layer or a further auxiliary layer, is conveniently coated with a protective layer that may have a thickness of 0.1 to 100 μm, preferably 0.1 to 50 μm and, most preferably, 0.5 to 15 μm. Mainly suitable for use as protective material are plastic materials that are coated in a thin layer, either direct or with the aid of adhesive layers, on to the substrate or the topmost layer. It is expedient to choose mechanically and thermally stable plastic materials which have good surface properties and may be additionally modified, for example marked. The plastics materials may be thermoset and thermoplastic materials. Radiation-cured (e.g. UV cured) protective layers which are particularly easy and economical to prepare are preferred. A host of radiation-curable materials are known. Exemplary radiation-curable monomers and oligomers are acrylates and methacrylates of diols, triols and tetrols, polyimides from aromatic tetracarboxylic acids and aromatic diamines containing $C_1$–$C_4$alkyl groups in at least two ortho-positions of the amino groups, and oligomers containing dialkyl groups, conveniently dimethylmaleimidyl groups. Specific examples are UV-crosslinkable polymers derived from polyacrylates, such as RENGOLUX® RZ 3200/003 or 3203/001, available from Morton International-Dr. Renger.

The memory-active layer may be a homogeneous mixture of compounds of formulae I and/or IV with a transparent binder, typically a plastic material. The thickness of the layer of the mixture and binder (applied conveniently by spin coater) may typically be from 0.1 to 100 μm, preferably from 0.5 to 50 μm and, most preferably, from 0.5 to 5 μm. The mixture with the binder can contain 0.1 to 95%, preferably 1 to 80% by weight and, most preferably 1 to 60% by weight, of compounds of formulae I and/or IV, based on the total amount of binder and solvent. Transparent binders may suitably be the plastic materials mentioned above in connection with the substrate. Particularly preferred binders are polycarbonates as well as polymethacrylates, thermoset polyesters and epoxy resins. The mixture may also be the substrate itself, typically a polycarbonate with which the compounds of formulae I and/or IV have been blended.

The recording materials used in the practice of this invention can be prepared by methods which are known per se. Depending on the materials used and their mode of use, different coating techniques can be applied.

Suitable coating techniques include immersion, casting, brushing, doctor coating, centrifugal casting, and vapour deposition methods which are carried out under a high vacuum. If, for example, casting methods are employed, then it is common practice to use solutions in organic solvents which may additionally contain a binder if the organic compound is solid. When using solvents, care must be taken that the substrates are inactive to these solvents. It is preferred to prepare all layers by vapour deposition, especially under vacuum. Suitable coating techniques are described, inter alia, in EP-A-0 401 791.

The recording layer or layers and the metallic reflective layers are preferably applied by vapour deposition under vacuum. The material to be applied is first put into a suitable vessel, which may be equipped with a resistance heating, and placed into a vacuum chamber. The substrate on to which the material is to be deposited is clamped above the vessel with the material to be vapourised. The clamp is constructed such that the substrate can be rotated (e.g. at 10 rpm) and heated. The vacuum chamber is evacuated to about $1.3 \cdot 10^{-5}$ to $1.3 \cdot 10^{-6}$ mbar ($10^{-5}$ to $10^{-6}$ torr), and the heating is adjusted such that the temperature of the material to be deposited rises to its vapourising temperature. The deposition is continued until the layer applied has the desired thickness. Depending on the structure of the system, first the recording material and then the reflective layer is applied, or conversely. The application of a reflective layer can in some cases be dispensed with. It is particularly preferred to apply the metallic reflective layer by the sputtering technique on account of the good bonding to the substrate. The material to be applied (e.g. aluminium) in the form of a plate is used as a "target" electrode, whereas the substrate is mounted on the counter-electrode. First the vacuum chamber is evacuated to about $10^{-6}$ torr and then inert gas, e.g. argon, is introduced until the pressure is about $10^{-3}$ torr. Between the target electrode and the counter-electrode a high direct current voltage or radio-frequency voltage of several kV is applied, optionally using permanent magnets (magnetron sputtering) so as to produce $Ar^+$ plasma. The metal particles sputtered by the $Ar^+$ ions of the target electrode are uniformly and firmly deposited on the substrate. Coating is effected within a few to several minutes, depending on the target materials, sputtering technique and sputtering conditions. This sputtering technique is described in detail in the technical literature (e.g. W. Kern and L. Vossen, "Thin Film Processes", Academic Press, 1978).

The thickness of the layer formed by vapour deposition can be monitored with the aid of an optical system which measures the reflectivity of the reflective surface coated with the absorption material. The growth of the layer thickness will preferably be monitored with a quartz resonator.

Protective layers and techniques for applying them are known. Such layers are usually organic polymers which can be thermoplastic or crosslinked. It is preferred to use photocured polymers which can be prepared from photocurable monomers or oligomers. Illustrative examples of photocurable monomers and oligomers are acrylates and methacrylates of diols, triols and tetrols. The layers can be prepared by spraying or casting techniques. They are preferably applied by spin coaters.

The structure of the recording material of this invention will depend mainly on the method of reading out: known techniques are measuring the change in transmission or reflection. If the recording system functions according to a change in light transmission, the structure may suitably comprise: transparent substrate/recording layer (one or more layers) and, if appropriate, transparent protective layer. The radiation for writing and reading out information can be applied either from the substrate side of the system or from the recording layer or protective layer side, the light detector always being on the adjacent side.

If the recording material is structured in accordance with the change in reflectivity, then the following other structures may be used: transparent substrate/recording layer (one or more layers)/reflective layer/and, if appropriate, protective layer (not necessarily transparent), or substrate (not necessarily transparent)/reflective layer/recording layer and, if appropriate, transparent protective layer. In the former case, the radiation is applied from the substrate side of the system, whereas in the latter case the radiation is applied from the recording layer or, if present, from the protective layer side of the system. In both cases, the light detector is on the same side as the light source. The first mentioned layer structure of the inventive recording material is generally preferred.

The material eligible for use in the practice of this invention is pre-eminently suitable for writing information by irradiation with laser light in the NIR range. After irradiation a markedly reduced absorption is observed. The change in reflection or transmission can therefore be used for reading out information without the stored information being destroyed by the laser light used for reading out. The information can therefore be read out repeatedly.

Suitable lasers include commercial diode lasers, preferably semiconductor diode lasers, for example GaAsAl, InGaAlP or GaAs lasers with a wavelength of 780, 650 and 830 nm respectively. The information can be written point by point using a light modulator.

The energy of the laser light used for recording may be typically from 0.1 to 10 nJ/marking (bit), preferably from 0.2 to 5 nJ/marking (bit) and, most preferably, 0.8 to 3 nJ/marking (bit). The amount of energy is essentially controlled by the irradiation time, for example by pulses in the range from a few microseconds, typically from 10 to 100 nanoseconds.

The recording material of this invention makes it possible to store information with a high degree of reliability and durability, the information being distinguished by very good mechanical and thermal stability as well as by superior light stability and clear edge definition. Particular advantages are the superior light sensitivity and the surprisingly high signal-to-noise ratio of carrier material to information marking, which permits the information to be read out easily. In addition, the optical recording system is simple and inexpensive. The information can be written by scanned, holographic or photographic exposure of the memory-active layer. The information is read out by measuring the absorption by the reflection or transmission method using laser light. It is particularly advantageous that laser light of the wavelength used for recording can be utilised, i.e. a second laser need not also be used. In a preferred embodiment of the process, information is written and read out at the same wavelength. The information is normally read out by using low-energy lasers whose radiation intensity is ten- to fifty-fold lower than the laser light used for recording. The information can be read out once or repeatedly. The shift in the absorption spectrum and/or the stored information can be read out with a photodetector using a low-energy laser. Suitable photodetectors comprise PIN photodiodes which make it possible to measure the spectral changes by transmission or absorption and, in particular, reflection.

The recording material of this invention may have the following structure:

(a) transparent substrate, (b) recording layer, and (c) transparent protective layer; or (a) transparent substrate, (b) recording layer, (c) reflective layer, and (d) protective layer; or (a) substrate, (b) reflective layer, (c) recording layer, and (d) transparent protective layer.

The invention further relates to a process for recording images, preferably for the optical recording and storage of information in the form of bits, which process comprises subjecting a novel recording material of this invention imagewise to heat or to heat radiation or point by point or linearly to laser light in the NIR range.

The invention relates in yet another of its aspects to a material which contains information, such that the recording layer of a novel recording material has applied thereto or written thereon images or marks in the form of bits that exhibit in the near infra-red range a diminished reflectance and increased absorption to the unchanged environment.

The invention further relates to a thermochromic composition that contains as thermochromic component at least one compound of formula (I) and/or at least one compound of formula IV. The composition preferably contains said thermochromic component in an amount of 0.001 to 20% by weight, based on the composition.

The invention also relates to a thermochromic composition comprising a) a colourless organic solvent, a polymer or an organic glass, and b) dissolved, blended with or present as layer on at least one surface, at least one compound of formula I and or at least one compound of formula IV. The composition preferably contains the compounds of formulae I and IV in an amount of 0.001 to 20% by weight, based on component a).

The invention further relates to the use of compounds of formulae I or IV as irreversible thermochromic systems for contrast formation, light absorption and thermochromic colour indicators.

The invention further relates to the use of a compound of formula I or IV for the irreversible optical storage of information, said information being written in a memory-active layer containing said compound by heat irradiation, preferably with IR laser light.

The invention also relates to the use of the compound of formula I or IV as active component in thermochromic display elements.

The invention also relates to the use of the compound of formula I or IV as thermochromic active component for imaging techniques by means of heat or heat radiation.

The novel compounds and/or materials of this invention make it possible to fabricate CD-compatible optical recording materials which find utility as computer memories, as photographic memories or as sound carriers. In addition, it is possible to fabricate display elements as well as thermo-photographs and thermographic prints.

The invention is illustrated in more detail by the following Examples.

A) Preparative Examples

Example A1: 3-(Imidazol-2-ylthio)phthalodinitrile

With stirring, 5.79 g (57.8 mmol) of 2-mercaptoimidazole, 23.97 g (173.4 mmol) of $K_2CO_3$ and 70 ml of DMSO are cooled to 15° C. Then a solution of 10.0 g (57.8 mmol) of 3-nitrophthalodinitrile in 30 ml of DMSO is aded dropwise over 15 minutes while keeping the temperature at 15° C. The mixture is then slowly warmed to 25° C. and stirred for 1 hour at 25° C. The mixture is poured into 18 ml of glacial acetic acid in 500 ml of water, while expelling nitrous gases with nitrogen. The reaction mixture is stirred for 15 minutes at 10° C., the precipitate is isolated by filtration and washed twice with water. The product is dissolved in tetrahydrofuran/toluene and the solution is dried over $Na_2SO_4$ and concentrated by evaporation. The residue is recrystallised from dioxane, giving 8.54 g (65% of theory) of pure 3-(imidazol-2-ylthio)phthalodinitrile.

Elemental analysis: $C_{11}H_6N_4S$ (MW 226.26) calcd: C 58.39 H 2.67 N 24.76 S 14.17 found: C 58.71 H 2.76 N 24.56 S 13.81

Mass spectrum (m/e): 226 ($M^+$, base peak).

When heated, the substance turns yellow, then green and finally black.

The following compounds are obtained in analogous manner at a reaction temperature of 25° C.:

Example A2:

3-(4,5-Dimethylimidazol-2-ylthio)phthalodinitrile (reaction time: 25 minutes; MS: 254 (base peak); Yield: 50% of theory). When heated, the substance turns yellow, then green and finally black.

Example A3:

3-(4-Phenylimidazol-2-ylthio)phthalodinitrile (reaction time: 15 minutes; MS: 302 (base peak); Yield: 40% of theory; mixture of tautomers). When heated, the substance turns yellow, then green and finally black.

Example A4:

3-(4,5-Diphenylimidazol-2-ylthio)phthalodinitrile (reaction time: 45 minutes; MS: 378 (base peak); Yield: 79% of theory). When heated, the substance turns yellow, then green and finally black.

Example A5:

3-(Benzimidazol-2-ylthio)phthalodinitrile (reaction time: 80 minutes; MS: 276 (base peak); Yield: 24% of theory). When heated, the substance turns yellow, then green and finally black.

Example A6:

3-(5-Methylbenzimidazol-2-ylthio)phthalodinitrile (reaction time: 60 minutes; MS: 290 (base peak); Yield: 20% of theory; mixture of tautomers). When heated, the substance turns yellow, then green and finally black.

Example A7:

3-(1 (H)- 1,2,4-Triazol-3-ylthio)phthalodinitrile (reaction time: 90 minutes; MS: 227 (base peak); Yield: 37% of theory; 3 tautomers are possible; the NMR spectrum shows 1 main component). When heated, the substance turns yellow, then green and finally black.

Example A8:

3-(5-Trifluoromethyl-1 (H)-1,2,4-triazol-3-ylthio)phthalodinitrile (reaction time: 60 minutes; MS: 295 (base peak); Yield: <10% of theory; probably mixture of tautomers). When heated, the substance undergoes a colour change to yellow, then green and finally black.

Example A9:
3-(Imidazol-2-ylthio)-5-nitrophthalodinitrile 0.92 g (9.17 mmol) of 2-mercaptoimidazole, 3.80 g (27.52 mmol) of $K_2CO_3$ and 15 ml of tetrahydrofuran are cooled in an ice/dry ice bath to −5° C. A solution of 2.0 g (9.17 mmol) of 3,5-dinitrophthalodinitrile in 10 ml of tetrahydrofuran is then added dropwise to the suspension. The mixture is thereafter added to a solution of 3 ml of glacial acetic acid in 200 ml of water. The resultant emulsion is extracted with tetrahydrofuran/toluene. The combined extracts are dried over $Na_2SO_4$ and concentrated by evaporation at a temperature not exceeding 60° C. The residue is recrystallised from tetrahydrofuran/toluene, giving 1.43 g (57% of theory) of crude 3-(imidazol-2-ylthio)-5-nitrophthalodinitrile, which is taken up in acetone/methylene chloride. The solution is filtered over silica gel and the filtrate is concentrated by evaporation, giving 1.17 g (47% of theory) of pure product.

Elemental analysis: $C_{11}H_5N_5O_2S$ (MG 271.26): calcd: C 48.71 H 1.86 N 25.82 O 11.80 S 11.82 found: C 48.86 H 2.02 N 25.56 O 12.18 S 11.63

Mass spectrum (m/e): 271 (M+; base peak)

When heated, the substance turns yellowish, then olive-green to black.

Example A10:
3-(Imidazol-2-ylthio)-5-methylthiophthalodinitrile

To a solution of 0.40 g (1.47 mmol) of 3-(imidazol-2-ylthio)-5-nitrophthalodinitrile in 5 ml of DMSO are added 0.10 g (1.47 mmol) of sodium methylmercaptide at 15° C. The reaction mixture is then stirred for 15 minutes at 15° C. and then poured into a solution of 1 ml of glacial acetic acid in 30 ml of water. The resultant emulsion is extracted with tetrahydrofuran/toluene. The combined extracts are dried over $Na_2SO_4$ and concentrated by evaporation at a temperature not exceeding 60° C. The residue (0.38 g; 95% of theory) is dissolved in 15% of acetone/85% of methylene chloride and chromatographed over silica gel. The fractions containing the product are concentrated by evaporation and the residue is recrystallised from tetrahydrofuran/toluene, giving 0.18 g (45% of theory) of pure 3-(imidazol-2-ylthio)-5-nitrophthalodinitrile.

MS (M/e): 272 (M+; base peak)

When heated, the substance turns first greenish-brown and then black.

Example A11:
3-(imidazol-2-ylthio)-5-isobutylthiophthalodinitrile

With stirring, 0.92 g (9.17 mmol) of 2-mercaptoimidazole, 5.07 g (36.7 mmol) of $K_2CO_3$ and 15 ml of tetrahydrofuran are cooled to −8° C. With stirring and cooling, a solution of 2.0 g (9.17 mmol) of 3,5-dinitrophthalodinitrile in 7 ml of tetrahydrofuran is slowly added dropwise and the reaction mixture is stirred for 30 minutes at 0°–5° C. The resultant 3-(imidazol-2-ylthio)-5-nitrophthalodinitrile is then further reacted direct by the dropwise addition of 0.99 g (11.01 mmol) of isobutyl mercaptan and further stirring for 20 minutes at 5° C. The reaction mixture is then poured into a solution of 7 ml of glacial acetic acid in 200 ml of water and extracted with methylene chloride. The combined extracts are dried over $Na_2SO_4$ and chromatographed over silica gel with methylene chlorid. The crude product (0.5 g; 20% of theory) is recrystallised from diethyl ether, affording 0.12 g (4% of theory) of 3-(imidazol-2-ylthio)-5-isobutylthiophthalodinitrile.

MS (m/e): 314 (M+); 258 (base peak)

When heated, the substance turns yellow, then green and, finally, black.

Example A12:
3-(Imidazol-2-ylthio)-5-phenylthiophthalodinitrile

To a solution of 0.40 g (1.47 mmol) of 3-(imidazol-2-ylthio)-5-nitrophthalodinitrile in 5 ml of DMSO are added 0.20 g (1.77 mmol) of thiophenol and 0.51 g (3.69 mmol) of $K_2CO_3$ at 15° C. The reaction mixture is stirred for 15 minutes at 15° C. and then poured into a solution of 1 ml of glacial acetic acid and 30 ml of water. The resultant emulsion is extracted with tetrahydrofuran/toluene. The combined extracts are washed with water, dried over $Na_2SO_4$ and concentrated by evaporation under vacuum at a temperature not exceeding 60° C. The residue is chromatographed with 15% acetone in methylene chloride over silica gel. The fractions containing the product are concentrated by evaporation, giving 0.15 g (31% of theory) of pure 3-(imidazol-2-ylthio)-5-phenylthiophthalodinitrile.

MS (m/e): 334 (M+; base peak).

When heated, the substance turns brownish-olive, then olive-green and, finally, black.

Example A13: 3-(Imidazol-2-ylthio)-5-(3-methoxyphenylthio)phthalodinitrile

With stirring, 0.92 g (9.17 mmol) of 2-mercaptoimidazole, 5.07 g (36.7 mmol) of $K_2CO_3$ and 15 ml of tetrahydrofuran are cooled to 0° C. Then a solution of 2.0 g of 3,5-dinitrophthalodinitrile in 7 ml of tetrahydrofuran is added dropwise at 0° C. over 10 minutes. The reaction mixture is thereafter stirred for 15 minutes at 0° C. The resultant 3-(imidazol-2-ylthio)-5-nitrophthalodinitrile is then further reacted direct by the dropwise addition of 1.42 g (10.09 mmol) of 3-methoxythiophenol. When the dropwise addition is complete, stirring is continued for 10 minutes at 0° C. The reaction mixture is then poured into a solution of 7 ml of glacial acetic acid in 200 ml of water and extracted with methylene chloride. The combined extracts are dried over $Na_2SO_4$ and concentrated by evaporation at a temperature not exceeding 40° C. The residue is chromatographed with 15% acetone in methylene chloride and recrystallised from diethyl ether, giving 0.59 g (18% of theory) of pure 3-(imidazol-2-ylthio)-5-phenylthiophthalodinitrile.

MS (m/e): 364 (M+; base peak).

When heated, the substance turns yellowish-green, then green and, finally, black.

Example A14:

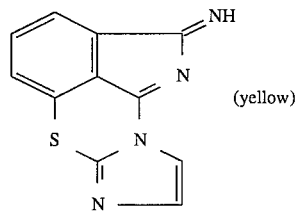

Compound 1
(yellow)

2.50 g (11.05 mmol) of 3-(imidazol-2-ylthio)phthalodinitrile are refluxed in 200 ml of o-dichlorobenzene for 2 hours. The mixture is then cooled and chromatographed over silica gel with methylene chloride and increasing amounts of acetone. The fractions containing the product are then concentrated by evaporation and the residue (1.45 g; 28% of theory) is sublimed at 190° C./1 torr, giving 0.71 g (28% of theory) of pure compound as sublimate.

MS (m/e): 226 (M+; base peak).

The NMR spectrum shows a mixture of syn/anti-NH

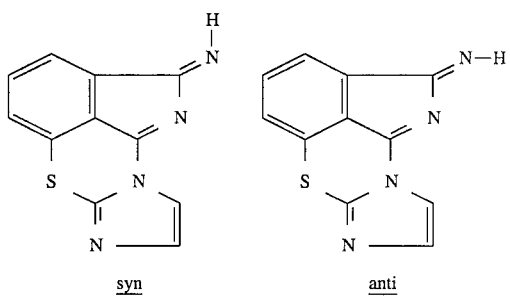

syn          anti in the ratio of ≅3:2 or 2:3.

UV/VIS spectrum ($\lambda_{max}/\epsilon$; DMF): 386/5200

The IR spectrum (KBr; $CH_2Cl_2$) shows no nitrile groups.

When heated, the compound turns yellow, then green and, finally, black.

Example A15:

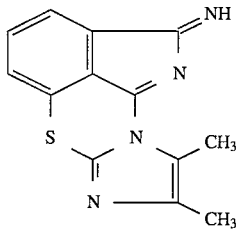

Compound 2

Following the procedure described in Example A14, 3-(3,4-dimethylimidazol-2-ylthio)phthalodinitrile are refluxed for 4 hours in xylene to give a syn/anti-mixture of compound 2. Yield: 29% of theory; MS (m/e): 254 (M+; base peak).

When heated, the substance turns yellow, then green and, finally, black.

Example A16:

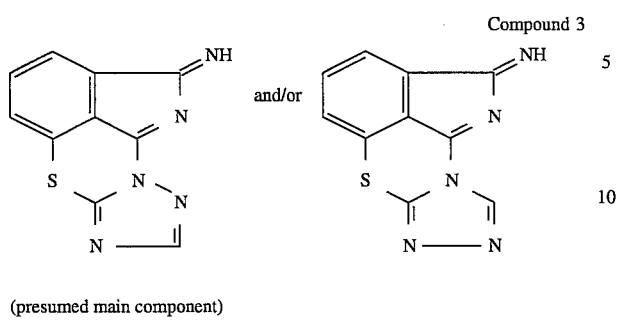

(presumed main component)

Following the procedure described in Example A14, 3-(1 (H)- 1,2,4-triazol-5-ylthio)phthalodinitrile are refluxed for 4 hours in mesitylene to give a syn/anti-mixture of compound 3. Yield: 14% of theory; MS (m/e): 227 (M+; base peak).

When heated, the substance turns yellow, then green and, finally, black.

Example A 17:

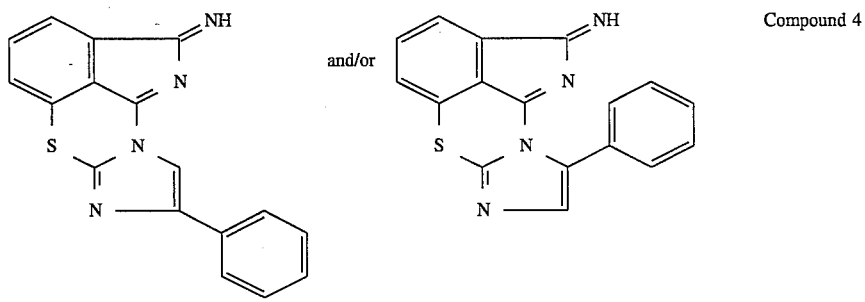

(presumed main component)

Following the procedure described in Example 7, 3-(4-phenylimidazol-2-ylthio)phthalodinitrile are refluxed for 9 hours in mesitylene to give a syn/anti-mixture of compound 4.

Yield: 23% of theory; MS (m/e): 302 (M+; base peak).

When heated, the compound first turns yellow, then green and, finally, black.

B) Use Examples

Example B1:

A 3.5% solution of 3-(imidazol-2-ylthio)-5-phenylthiophthalodinitrile (q.v. Example A12) in tetrahydrofuran is spin-coated at 250 rpm on to a glass substrate. After drying, the layer thickness of the film so obtained is 0.42 μm. The yellowish film exhibits low absorption in the wavelength range 400 nm-900 nm (decadal absorption coefficient <0.1 ). After heating for 5 minutes at 250° C.; an amorphous, dark-olive layer forms which has a very broad band absorption in the indicated wavelength range (maximum absorption coefficient 0.8).

Example B2:

A 5% solution of 3-(imidazol-2-ylthio)-5-isobutylthiophthalodinitrile (q.v. Example A11) is spin-coated on to a glass substrate. The dried film exhibits low absorption in the wavelength range 500 nm-900 nm (decadal absorption coefficient <0.05). After a heat treatment for 15 minutes at 200° C., the colour changes from yellow to dark olive with strong absorption in the visible and near infra-red range with maximum absorption at 680 nm.

What is claimed is:

1. A compound of formula I

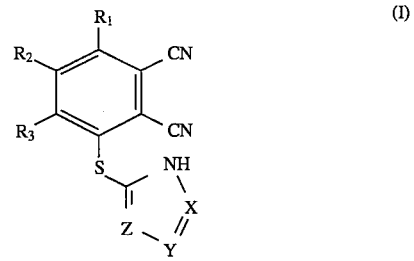

wherein $R_1$, $R_2$ and $R_3$ are each independently of one another hydrogen, a straight-chain or branched $C_1$-$C_{12}$alkyl group, which is unsubstituted or substituted by alkoxy, alkylthio, aryloxy, arylthio, halogen, —CN, —COOH, —COOR$_7$, —NR$_8$R$_9$ or —CONR$_8$R$_9$, a $C_1$-$C_{12}$alkoxy group in which the alkyl moiety is straight-chain or branched and unsubstituted or substituted by alkoxy, alkylthio, aryloxy, arylthio, halogen, —CN, —COOH, —COOR$_7$, —NR$_8$R$_9$ or —CONR$_8$R$_9$, a $C_1$-$C_{12}$alkylthio group in which the alkyl moiety is straight-chain or branched and unsubstituted or substituted by alkoxy, alkylthio, aryloxy, arylthio, halogen, —CN, —COOH, —COOR$_7$, —NR$_8$R$_9$ or —CONR$_8$R$_9$, a $C_5$-$C_8$cycloalkyl group which is unsubstituted or substituted by alkyl, alkoxy, alkylthio, aryloxy, arylthio, halogen, —CN, —COOH, —COOR$_7$, —NR$_8$R$_9$ or —CONR$_8$R$_9$, a $C_5$-$C_8$cycloalkoxy group which is unsubstituted or substituted by alkyl, alkoxy, alkylthio, aryloxy, arylthio, halogen, —CN, —COOH, —COOR$_7$, —NR$_8$R$_9$ or —CONR$_8$R$_9$, a $C_5$-$C_8$cycloalkylthio group which is unsubstituted or substituted by alkyl, alkoxy, alkylthio, aryloxy, arylthio, halogen, —CN, —COOH, —COOR$_7$, —NR$_8$R$_9$ or —CONR$_8$R$_9$, a $C_6$-$C_{10}$aryl group which is unsubstituted or substituted by alkyl, alkoxy, alkylthio, aryloxy, arylthio, halogen, —CN, —COOH, —COOR$_7$, —NR$_8$R$_9$ or —CONR$_8$R$_9$, a $C_6$-$C_{10}$aryloxy group in which the aryl moiety is unsubstituted or substituted by alkyl, alkoxy, alkylthio, phenyl, phenoxy, phenylthio, halogen, —CN, —COOH, —COOR$_7$, —NR$_8$R$_9$ or 13 CONR$_8$R$_9$, a $C_6$-$C_{10}$arylthio group in which the aryl moiety is unsubstituted or substituted by alkyl, alkoxy, alkylthio, phenyl, phenoxy, phenylthio, halogen, —CN, —COOH, —COOR$_7$, —NR$_8$R$_9$ or —CONR$_8$R$_9$ or $R_1$, $R_2$, $R_3$ are independently of one another nitro, halogen, cyano, —COOH, —COOR$_7$, —NR$_8$R$_9$ or-CONR$_8$R$_9$, and wherein $R_7$ is $C_1$-$C_{20}$alkyl, $C_5$-$C_8$cycloalkyl, phenyl or phenyl-$C_1$-$C_4$alkyl, and $R_8$ and $R_9$ are each independently of the other hydrogen, $C_1$-$C_8$alkyl, phenyl or phenyl-$C_1$-$C_4$alkyl; X is nitrogen or $CR_4$, Y is nitrogen or $CR_5$ and Z is nitrogen or $CR_6$, and $R_4$, $R_5$ and $R_6$ are each independently of one another hydrogen, a straight-chain or branched $C_1$-$C_{12}$alkyl group which is unsubstituted or substituted by alkoxy, alkylthio, aryloxy, arylthio, halogen, —CN, —COOH, —COOR$_7$, —NR$_8$R$_9$ or —CONR$_8$R$_9$, or a $C_6$-$C_{10}$aryl group which is unsubstituted or substituted by alkyl, alkoxy, alkylthio, aryloxy, arylthio, halogen, —CN, —COOH, —COOR$_7$, —NR$_8$R$_9$ or —CONR$_8$R$_9$, or when X is $CR_4$ and Y is $CR_5$ and Z is nitrogen or $CR_6$, or when Y is $CR_5$ and Z is $CR_6$ and X is nitrogen or $CR_4$, then each pair of substituents $R_4$ and $R_5$ and $R_5$ and $R_6$ forms a group

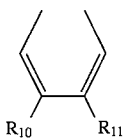

or a tetramethylene group, substituted by $R_{10}$ and $R_{11}$ wherein $R_{10}$ and $R_{11}$ are each independently of the other hydrogen, $C_1$-$C_6$alkyl, phenyl or phenyl-$C_1$-$C_4$alkyl.

2. A compound according to claim 1, wherein $R_1$, $R_2$ and $R_3$ are each independently of one another hydrogen, a $C_1$-$C_8$alkyl group which is unsubstituted or substituted by $C_1$-$C_4$alkoxy, $C_1$-$C_4$alkylthio, phenyl, phenoxy, phenylthio, fluoro, chloro, bromo, —CN, —COOH, —COOR$_7$, —NR$_8$R$_9$ or —CONR$_8$R$_9$; a $C_1$-$C_8$alkoxy group in which the the alkyl moiety is straight-chain or branched and is unsubstituted or substituted by $C_1$-$C_4$alkoxy, $C_1$-$C_4$alkylthio, phenyl, phenoxy, phenylthio, fluoro, chloro, bromo, —CN, —COOH, —COOR$_7$, —NR$_8$R$_9$ or —CONR$_8$R$_9$; a $C_1$-$C_8$alkylthio group in which the alkyl moiety is straight-chain or branched and is unsubstituted or substituted by $C_1$-$C_4$alkoxy, $C_1$-$C_4$alkylthio, phenyl, phenoxy, phenylthio, fluoro, chloro, bromo, —CN, —COOH, —COOR$_7$, —NR$_8$R$_9$ or —CONR$_8$R$_9$; a cyclohexyloxy group which is unsubstituted or substituted by $C_1$-$C_4$alkyl, $C_1$-$C_4$alkoxy, $C_1$-$C_4$alkylthio phenyl, phenoxy, phenylthio, fluoro, chloro, bromo, —CN, —COOH, —COOR$_7$, —NR$_8$R$_9$ or —CONR$_8$R$_9$; a cyclohexyloxy group which is unsubstituted or substituted by $C_1$-$C_4$alkyl, $C_1$-$C_4$alkoxy, $C_1$-$C_4$alkylthio, phenyl, phenoxy, phenylthio, fluoro, chloro, bromo, —CN, —COOH, —COOR$_7$, —NR$_8$R$_9$ or —CONR$_8$R$_9$; a cyclohexylthio group which is unsubstituted or substituted by $C_1$-$C_4$alkyl, $C_1$-$C_4$alkoxy, $C_1$-$C_4$alkylthio, phenyl, phenoxy, phenylthio, fluoro, chloro, bromo, —CN, —COOH, —COOR$_7$, —NR$_8$R$_9$ or —CONR$_8$R$_9$; a phenyl or naphthyl group which is unsubstituted or substituted by $C_1$-$C_4$alkyl, $C_1$-$C_4$alkoxy, $C_1$-$C_4$alkylthio, phenyl, phenoxy, phenylthio, fluoro, chloro, bromo, —CN, —COOH, —COOR$_7$, —NR$_8$R$_9$ or —CONR$_8$R$_9$; a phenoxy or naphthoxy group which is unsubstituted or substituted by $C_1$-$C_4$alkyl, $C_1$-$C_4$alkoxy, $C_1$-$C_4$alkylthio, phenyl, phenoxy, phenylthio, fluoro, chloro, bromo, —CN, —COOH, —COOR$_7$, —NR$_8$R$_9$ or —CONR$_8$R$_9$; a phenylthio, or naphthylthio group which is unsubstituted or substituted by $C_1$-$C_4$alkyl, $C_1$-$C_4$alkoxy, $C_1$-$C_4$alkylthio, phenyl, phenoxy, phenylthio, fluoro, chloro, bromo, —CN, —COOH, —COOR$_7$, —NR$_8$R$_9$ or —CONR$_8$R$_9$; or fluoro, chloro, bromo, nitro, cyano, —COOH, —COOR$_6$, —NR$_7$R$_8$ or —CONR$_7$R$_8$, wherein $R_7$ is $C_1$-$C_8$alkyl or phenyl and $R_8$ and $R_9$ are each independently of the other hydrogen, $C_1$-$C_8$alkyl, phenyl or phenyl-$C_1$-$C_4$alkyl.

3. A compound according to claim 2, wherein $R_1$, $R_2$ and $R_3$ are each independently of one another hydrogen, a $C_1$-$C_4$alkyl group which is unsubstituted or substituted by $C_1$-$C_4$alkoxy, $C_1$-$C_4$alkylthio, phenyl, phenoxy, phenylthio, fluoro, chloro, bromo, —CN, —COOH, —COOR$_7$, —NR$_8$R$_9$ or —CONR$_8$R$_9$; a $C_1$-$C_4$alkoxy group in which the alkyl moiety is straight-chain or branched and which is unsubstituted or substituted by $C_1$-$C_4$alkoxy, $C_1$-$C_4$alkylthio, phenyl, phenoxy, phenylthio, fluoro, chloro, bromo, —CN, —COOH, —COOR$_7$, —NR$_8$R$_9$ or —CONR8R$_9$; a $C_1$-$C_4$alkylthio group in which the alkyl moiety is straight-chain or branched and which is unsubstituted or substituted by $C_1$-$C_4$alkoxy, $C_1$-$C_4$alkylthio, phenyl, phenoxy, phenylthio, fluoro, chloro, bromo, —CN, —COOH, —COOR$_7$, —NR$_8$R$_9$ or —CONR$_8$R$_9$; a cyclohexyl group which is unsubstituted or substituted by $C_1$-$C_4$alkyl, $C_1$-$C_4$alkoxy, $C_1$-$C_4$alkylthio, phenyl, phenoxy, phenylthio, fluoro, chloro, bromo, —CN, —COOH, —COOR$_7$, —NR$_8$R$_9$ or —CONR$_8$R$_9$; a cyclohexyloxy group which is unsubstituted or substituted by $C_1$-$C_4$alkyl, $C_1$-$C_4$alkoxy, $C_1$-$C_4$alkylthio, phenyl, phenoxy, phenylthio, fluoro, chloro, bromo, —CN, —COOH, —COOR$_7$, —NR$_8$R$_9$ or —CONR$_8$R$_9$; a cyclohexylthio group which is unsubstituted or substituted by $C_1$-$C_4$alkyl, $C_1$-$C_4$alkoxy, $C_1$-$C_4$alkylthio, phenyl, phenoxy, phenylthio, fluoro, chloro, bromo, —CN, —COOH, —COOR$_7$, —NR$_8$R$_9$ or —CONR$_8$R$_9$; a phenyl or naphthyl group which is unsubstituted or substituted by $C_1$-$C_4$alkyl, $C_1$-$C_4$alkoxy, $C_1$-$C_4$alkylthio, phenyl, phenoxy, phenylthio, fluoro, chloro, bromo, —CN, —COOH, —COOR$_7$, —NR$_8$R$_9$ or —CONR$_8$R$_9$; a phenoxy or naphthoxy group which is unsubstituted or substituted by $C_1$-$C_4$alkyl, $C_1$-$C_4$alkoxy, $C_1$-$C_4$alkylthio, phenyl, phenoxy, phenylthio, fluoro, chloro, bromo, —CN, —COOH, —COOR$_7$, —NR$_8$R$_9$ or —CONR$_8$R$_9$; a phenylthio or naphthylthio group which is unsubstituted or substituted by $C_1$-$C_4$alkyl, $C_1$-$C_4$alkoxy, $C_1$-$C_4$alkylthio, phenyl, phenoxy, phenylthio, fluoro, chloro, bromo, —CN, —COOH, —COOR$_7$, —NR$_8$R$_9$ or —CONR$_8$R$_9$; or fluoro, chloro, bromo, nitro, cyano, —COOH, —COOR$_6$, —NR$_7$R$_8$ or —CONR$_7$R$_8$, wherein $R_7$ is $C_1$-$C_4$alkyl or phenyl, and $R_8$ and $R_9$ are each independently of the other hydrogen, $C_1$-$C_4$alkyl, phenyl or benzyl.

4. A compound according to claim 1, wherein the group of formula

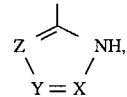

present in the compounds of formula I, wherein X is nitrogen or $CR_4$, Y is nitrogen or $CR_5$ and Z is nitrogen or $CR_6$, and $R_4$, $R_5$ and $R_6$ are as defined in claim 1, is pyrrol-2-yl, imidazol-2-yl, imidazol-4-yl, imidazol-5-yl, pyrazol-3-yl, pyrazol-5-yl, 1H-1,2,3-triazol-5-yl, 2H-1,2,3-triazol-5-yl, 3H-1,2,3-triazol-5-yl, 1H-1,2,4-triazol-5-yl, 2H-1,2,4-triazol-5-yl, 4H-1,2,4-triazol-5-yl, 1H-1,2,3,4-tetrazol-5-yl, 2H-1,2,3,4-tetrazol-5-yl, indol-2-yl, isoindol-1-yl, benzimidazol-2-yl, benzpyrazol-3-yl, 4,5,6,7-tetrahydroindol-2-yl, 4,5,6,7-tetrahydroisoindol-1-yl, 4,5,6,7-tetrahydrobenzimidazol-2-yl, 4,5,6,7-tetrahydrobenzpyrazol-3-yl, each unsubstituted or substituted by $R_4$, $R_5$ and $R_6$, in which radicals the fused benzene rings or tetrahydrobenzene rings may be substituted by $R_{10}$ and $R_{11}$, which have the meanings given in claim 1 in the definition of formula I.

5. A compound according to claim 1, wherein X is $CR_4$, Y is $CR_5$ and Z is $CR_6$, and $R_4$, $R_5$ and $R_6$ are each independently of one another $C_1$–$C_4$alkyl, $C_1$–$C_4$haloalkyl or phenyl, or each pair of substituents $R_4$ and $R_5$ or $R_5$ and $R_6$ is a group

.

6. A compound according to claim 1, wherein X is $CR_4$, Y is $CR_5$ and Z is nitrogen, and $R_4$ and $R_5$ are each independently of the other hydrogen, $C_1$–$C_4$alkyl, $C_1$–$C_4$haloalkyl or phenyl, or $R_4$ and $R_5$, taken together, are a group

.

7. A compound according to claim 1, wherein X is $CR_4$, Y is nitrogen and Z is $CR_6$, and $R_4$ and $R_6$ are each independently of the other hydrogen, $C_1$–$C_4$alkyl, $C_1$–$C_4$haloalkyl or phenyl.

8. A compound according to claim 1, wherein X is nitrogen, Y is $CR_5$ and Z is $CR_6$, and $R_5$ and $R_6$ are each independently of the other hydrogen, $C_1$–$C_4$alkyl, $C_1$–$C_4$haloalkyl or phenyl, or $R_5$ and $R_6$, taken together, are a 1,3-group

9. A compound according to claim 1, wherein X and Y are nitrogen, and Z is $CR_6$, and $R_6$ is hydrogen, $C_1$–$C_4$alkyl, $C_1$–$C_4$haloalkyl or phenyl.

10. A compound according to claim 1, wherein X, Y and Z are nitrogen.

11. A compound according to claim 1, wherein $R_1$ and $R_3$ are hydrogen and $R_2$, X, Y and Z are as defined in claim 1 in connection with formula I.

12. A compound according to claim 1, wherein $R_1$ and $R_3$ are hydrogen, $R_2$ is $C_1$–$C_8$alkyl, $C_1$–$C_8$alkoxy, $C_1$–$C_8$alkylthio, cyclohexyl, cyclohexyloxy, cyclohexylthio, phenyl, phenoxy, phenylthio, fluoro, chloro, bromo, nitro, cyano, —COOH, —COOR$_7$, —NR$_8$R$_9$ or —CONR$_8$R$_9$, where R$_7$ is $C_1$–$C_8$alkyl, phenyl-$C_1$–$C_4$alkyl or phenyl, and R$_8$ and R$_9$ are each independently of the other hydrogen, $C_1$–$C_8$alkyl, phenyl or phenyl-$C_1$–$C_4$alkyl, X is nitrogen or $CR_4$, Y is nitrogen or $CR_5$ and Z is nitrogen or $CR_6$, where $R_4$, $R_5$ and $R_6$ are each independently of one another hydrogen, $C_1$–$C_4$alkyl, $C_1$–$C_4$haloalkyl or phenyl, or when X is $CR_4$ and Y is $CR_5$ and Z is nitrogen or $CR_6$, or when Y is $CR_5$ and Z is $CR_6$ and X is nitrogen or $CR_4$, then each pair of substituents $R_4$ and $R_5$ or $R_5$ and $R_6$ is a group

13. A compound according to claim 1, wherein $R_1$ and $R_3$ are hydrogen and $R_2$ is $C_1$–$C_4$alkyl, $C_1$–$C_4$alkoxy, $C_1$–$C_4$alkylthio, cyclohexyl, cyclohexyloxy, cyclohexylthio, phenyl, phenoxy, phenylthio, fluoro, chloro, bromo, nitro, cyano, —COOH, —COOR$_7$, —NR$_8$R$_9$ or —CONR$_8$R$_9$, wherein R$_7$ is $C_1$–$C_4$alkyl, phenyl or benzyl, and R$_8$ and R$_9$ are each independently of the other hydrogen, $C_1$–$C_4$alkyl, phenyl or benzyl, X is nitrogen or $CR_4$, Y is nitrogen or $CR_5$ and Z is nitrogen or $CR_6$, where $R_4$, $R_5$ and $R_6$ are each independently of one another hydrogen, $C_1$–$C_4$alkyl, $C_1$–$C_4$haloalkyl or phenyl, or when X is $CR_4$ and Y is $CR_5$ and Z is nitrogen or $CR_6$, or when Y is $CR_5$ and Z is $CR_6$ and X is nitrogen or $CR_4$, then each pair of substituents $R_4$ and $R_5$ or $R_5$ and $R_6$ is a group 14. A compound according to claim 1, wherein $R_1$ and $R_3$ are hydrogen, $R_2$ is hydrogen, nitro, $C_1$–$C_4$alkylthio or phenylthio, in which the phenyl moiety is unsubstituted or is substituted by $C_1$–$C_4$alkyl, $C_1$–$C_4$alkoxy or $C_1$–$C_4$alkylthio, X is $CR_4$, Y is $CR_5$ or nitrogen, and Z is nitrogen, and $R_4$ and $R_5$ are each independently of the other hydrogen, $C_1$–$C_4$alkyl, $C_1$–$C_4$haloalkyl, phenyl or, taken together, are a group

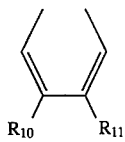

wherein $R_{10}$ and $R_{11}$ are each independently of the other hydrogen or $C_1$–$C_4$alkyl.

* * * * *